US00PP28091P3

(12) United States Plant Patent
Grosser

(10) Patent No.: US PP28,091 P3
(45) Date of Patent: Jun. 13, 2017

(54) ***CITRUS* ROOTSTOCK NAMED 'UFR-17'**

(50) Latin Name: [*Citrus reticulata/Citrus paradisi+Citrus grandis*]×[*Citrus aurantium+Citrus sinensis/Poncirus trifoliata*]
Varietal Denomination: UFR-17

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 116 days.

(21) Appl. No.: 14/545,063

(22) Filed: Mar. 20, 2015

(65) Prior Publication Data

US 2015/0271970 P1 Sep. 24, 2015

Related U.S. Application Data

(60) Provisional application No. 61/969,678, filed on Mar. 24, 2014.

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

PUBLICATIONS

PLUTO: Plant Variety Databse, Aug. 10, 2016, citation for 'UFR-17'.1 page.*
U.S. Appl. No. 14/544,424, filed Jan. 5, 2015, Grosser.
U.S. Appl. No. 14/544,425, filed Jan. 5, 2015, Grosser.
U.S. Appl. No. 14/544,423, filed Jan. 5, 2015, Grosser.
U.S. Appl. No. 14/544,427, filed Jan. 5, 2015, Grosser.
U.S. Appl. No. 14/544,570, filed Jan. 22, 2015, Grosser.
U.S. Appl. No. 14/544,572, filed Jan. 22, 2015, Grosser.
U.S. Appl. No. 14/544,571, filed Jan. 22, 2015, Grosser.
U.S. Appl. No. 14/544,573, filed Jan. 22, 2015, Grosser.
Grosser et al., "Protoplast fusion and citrus improvement," *Plant Breeding Reviews* 8:339-374, 1990.
Grosser et al., "Protoplast Fusion in the Production of Tetraploids and Triploids: Applications in Scion and Rootstock Breeding in Citrus," *Plant Cell Tissue and Organ Culture* 104:343-357, 2011.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora*-Diaprepes Complex via Greenhouse Screening," *Proc. Fla. State Hort. Soc.* 120:103-109, 2007.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UFR-17' is a new and distinct allotetraploid *citrus* rootstock for tree size control and improved disease resistance. 'UFR-17' has shown a positive reaction to Huanglongbing disease (HLB, or *citrus* greening disease) in multiple experimental field trials. Scion trees grafted on this rootstock show a reduced frequency of infection and reduced disease symptoms once infected as compared to commercial diploid rootstocks.

6 Drawing Sheets

Latin name of the genus and species of the plant claimed: *[Citrus reticulata/Citrus paradisi+Citrus grandis]×[Citrus aurantium+Citrus sinensis/Poncirus trifoliata].*

Variety denomination: 'UFR-17'.

BACKGROUND OF THE INVENTION

The present invention relates to a new and distinct variety of *citrus* rootstock named 'UFR-17'. The Plant Improvement Team in Lake Alfred, Fla. has pioneered the development and testing of allotetraploid *citrus* rootstocks. 'UFR-17' (identified as Green #2 in field trials) is an allotetraploid zygotic hybrid derived from a conventional cross of two somatic hybrids previously produced by protoplast fusion. The somatic hybrid seed parent is 'Nova' mandarin hybrid+ 'Hirado Buntan' pummelo (zygotic seedling), and the somatic hybrid pollen parent is sour orange+'Carrizo' citrange.

BRIEF SUMMARY OF THE INVENTION

'UFR-17' was selected on the basis of its positive reaction to Huanglongbing disease (HLB, or *citrus* greening disease) in multiple experimental field trials. Scion trees grafted onto this rootstock showed a reduced frequency of infection and reduced disease symptoms once infected when compared to other commercial diploid rootstocks. 'UFR-17' is seedy and polyembryonic, making it amenable to standard nursery propagation practices for uniform liner production. Because scion trees grafted onto 'UFR-17' grow off quickly and remain small to medium-sized, 'UFR-17' has potential use in Advanced *Citrus* Production Systems that feature high-density plantings. Long-term performance of trees grafted onto 'UFR-17' is unknown. Yield and fruit quality data is limited, but 4-year-old trees indicate good productivity in several locations, including ridge and flatwood sites. Tolerance to *citrus* blight is also unknown, but under investigation. The first asexual reproduction of 'UFR-17' was performed in Lake Alfred, Fla. by grafting buds of the original tree to 'Carrizo' citrange and 'Swingle' citrumelo rootstocks. Additional true-to-type trees have been propagated from these two grafted trees via rooted cuttings and by nucellar seed propagation.

BRIEF DESCRIPTION OF THE DRAWINGS

'UFR-17' is illustrated by the accompanying photographs, which show the tree form, foliage, and fruit. The colors shown are as true as can be reasonably obtained by conventional photographic procedures. The photographs are of a tree approximately 12 years old on 'Carrizo' citrange rootstock growing in Lake Alfred, Fla. All figures were taken in the fall of 2013 from the same tree.

DETAILED BOTANICAL DESCRIPTION

Figure 1:
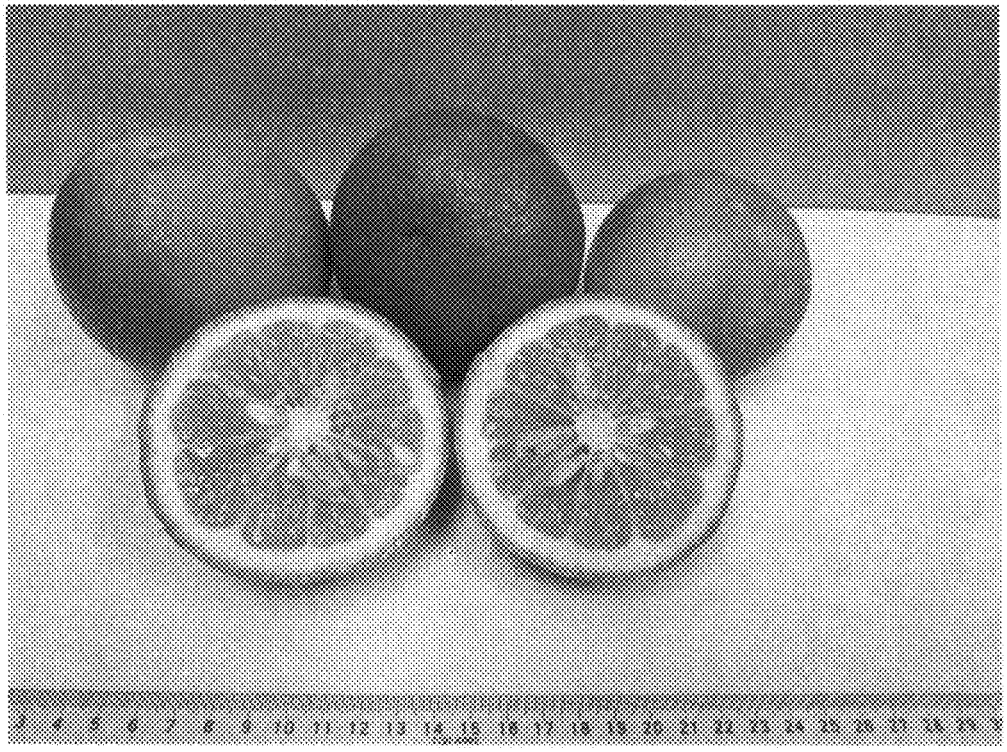
FIG. 1—Shows a close-up of the nearly mature fruits with the rind and cross-sectional view of the fruit when cut in the center.
Figure 2:
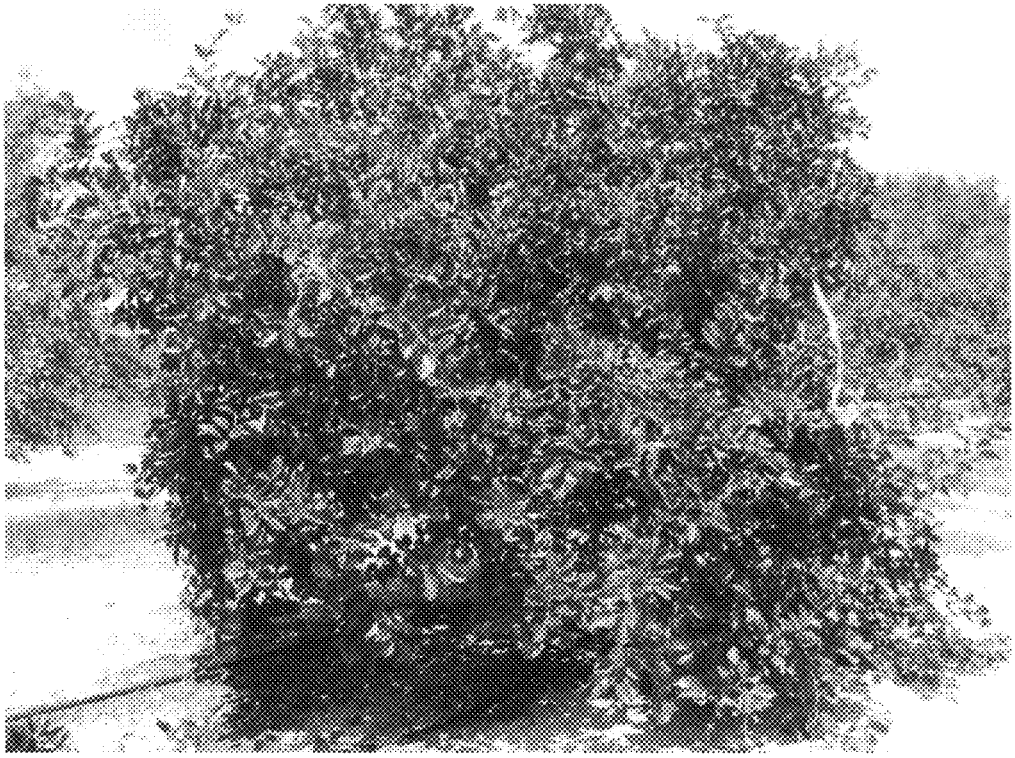
FIG. 2—Shows the overall mature plant growth habit.
Figure 3:
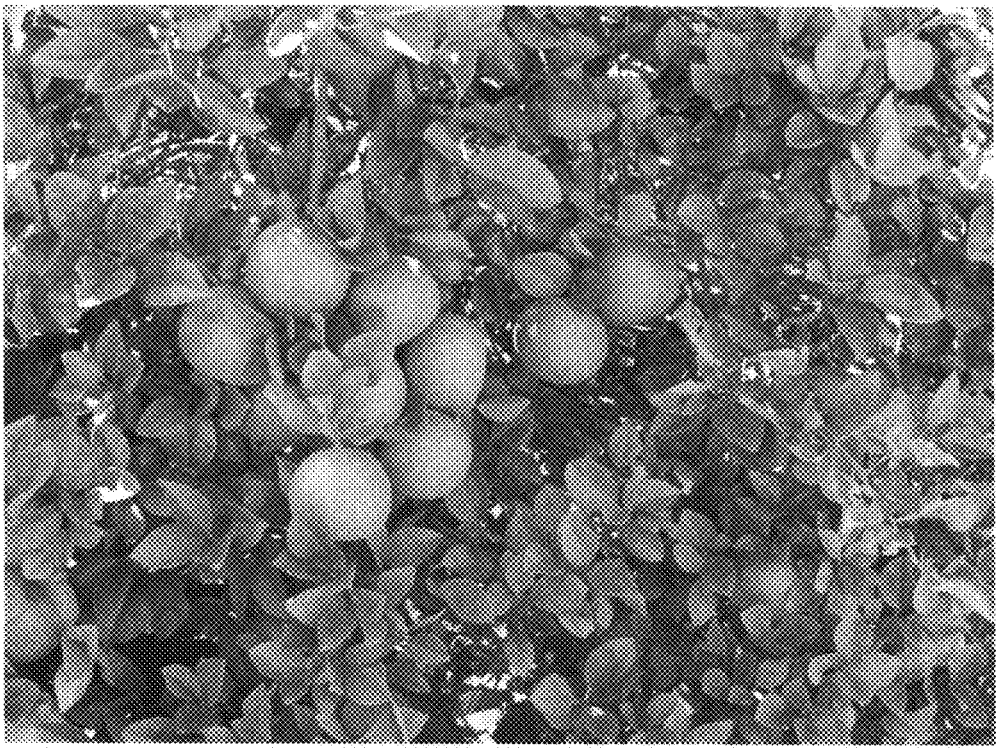
FIG. 3—Shows nearly mature fruits hanging on the tree.
Figure 4:
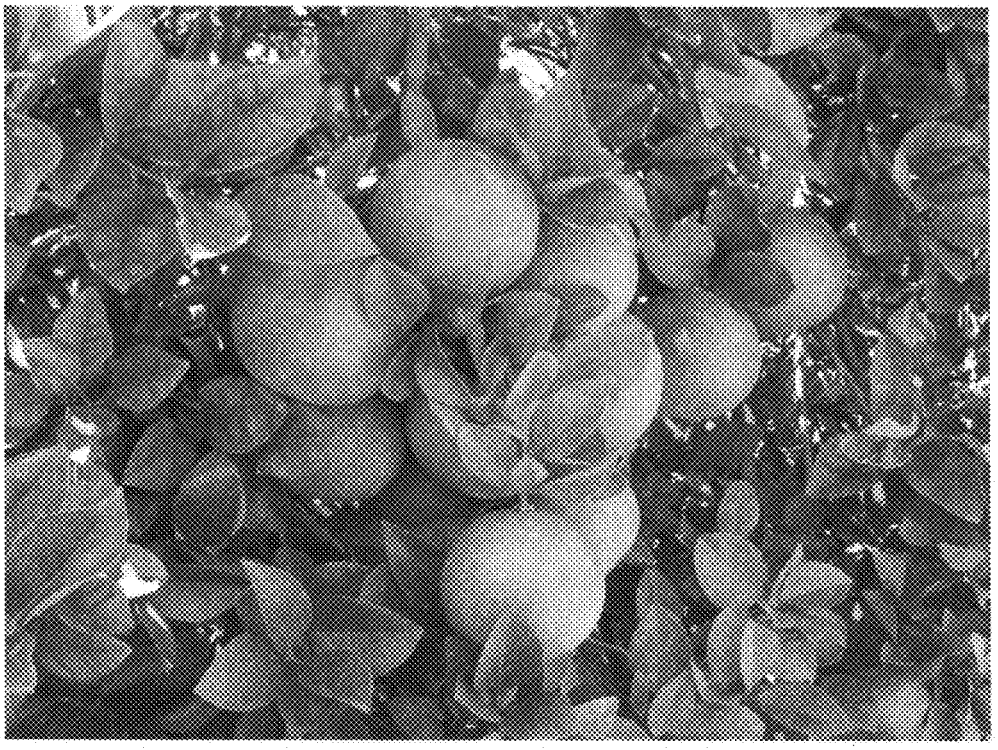
FIG. 4—Shows leaves and nearly mature fruits.
Figure 5:
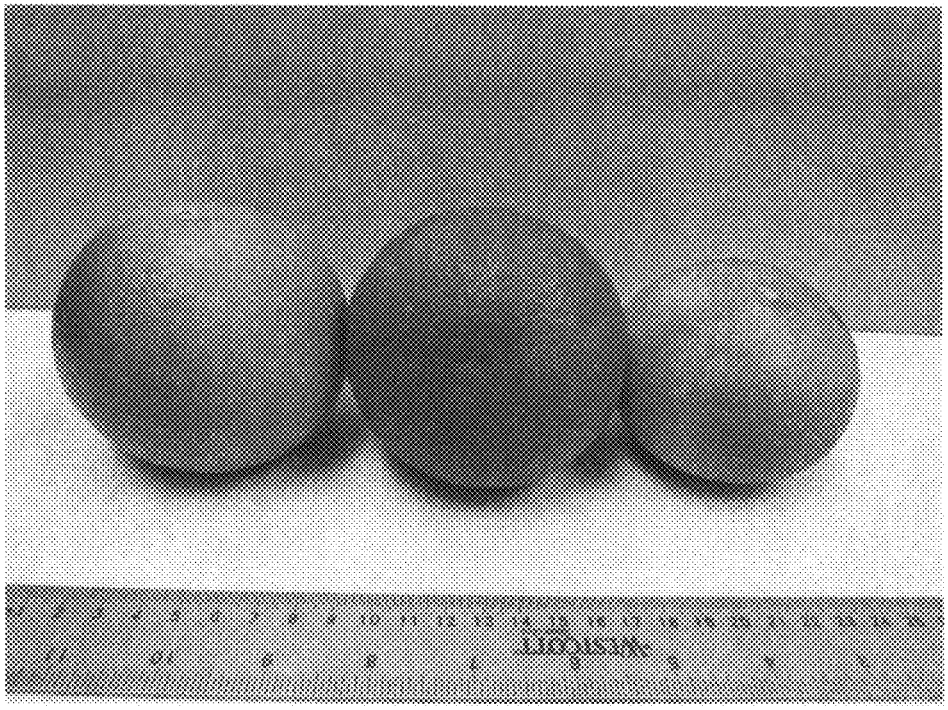
FIG. 5—Shows a close-up of nearly mature fruits.
Figure 6:
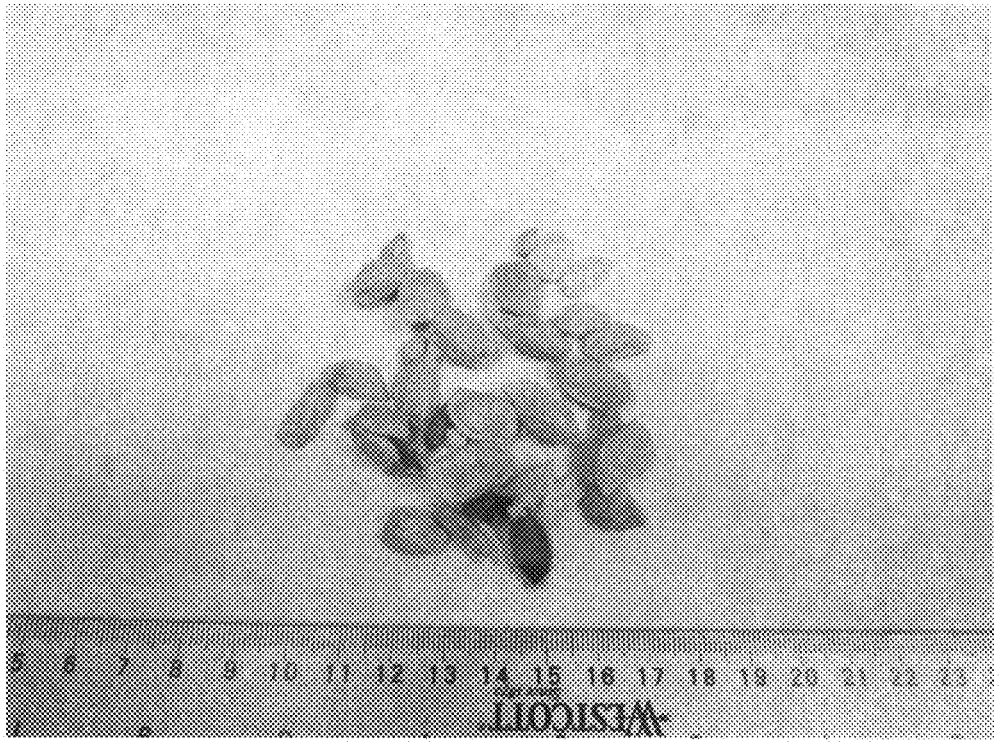
FIG. 6—Shows a close-up of seeds from nearly mature fruit.

The following detailed description sets forth the distinctive characteristics of 'UFR-17'. The colors (except those in common terms) are described from The R.H.S. Colour Chart published by The Royal Horticultural Society in London (second edition), in association with the Flower Council of Holland.

Phenotypic Description of *Citrus grandis*×*Citrus reticulata* 'UFR-17'

Classification:

*Botanical.*—*[Citrus reticulata/Citrus paradisi+Citrus grandis]×[Citrus aurantium+Citrus sinensis/Poncirus trifoliata].*

*Common name.*—*Citrus* Rootstock.

Parentage:

*Female parent.*—'Nova mandarin+Hirado Buntan zyg.' somatic hybrid (unpatented).

*Male parent.*—'Sour orange+Carrizo citrange' somatic hybrid (unpatented).

Tree:

*Ploidy.*—Tetraploid.

*Size.*—Medium.

*Height.*—3.5 meters.

*Tree spread.*—3.5 to 4.0 meters.

*Vigor.*—Vigorous.

*Density.*—Canopies are quite dense.

*Form.*—The tree is obloid-shaped with most lateral branches growing toward low to medium angles.

*Growth habit.*—Tree exhibits both upright and lateral growth.

Trunk:

*Trunk diameter.*—16.5 cm in diameter at 30 cm above the ground on a 12-year-old tree grafted to 'Carrizo' citrange rootstock.

*Trunk texture.*—Smooth.

*Trunk bark color.*—RHS 197A (greyed-green); irregularly striated with RHS N189 (greyed-green).

Branches:

*Crotch angle.*—First crotch forms a 40- to 45-degree angle; middle crotch forms a 90-degree angle.

*Branch length.*—Branch reaches 2.6 meters from the first crotch to the tip of the branch.

*Branch texture.*—Relatively smooth with occasional small thorns or spines.

*Branch color* (*shoots from previous flush, hardened, and* 4 *to* 5 *mm in diameter*).—RHS 137A (green).

Leaves:

*Size* (*lamina average*).—Length: 90.5 mm. Width: 61.6 mm. L/W ratio: 1.46.

*Thickness.*—Thicker than average diploid *citrus* rootstock hybrids.

*Type.*—Mostly simple leaf types, occasionally with bifoliate types of leaves appearing within the same tree.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS N137A (green). Lower surface (abaxial): RHS 146A (green).

*Petiole.*—Shape: Brevipetiolate (shorter than leaf lamina); junction between petiole and lamina is articulate. Width (petiole wing): Narrow. Shape (petiole wing): Obovate. Length: 21.6 to 24.6 mm. Width: 5.6 to 6.7 mm. Color: RHS N137A (green).

Flowers and flower buds:

*Type.*—Hermaphrodite.

*Bearing.*—Flowers grow from leaf axillaries and leaf terminals singly and in small clusters; most single flowers grow from leaf axillaries.

*Flower bud.*—Initial visible flower bud size: Length: 1.8 mm. Diameter: 2.4 mm. Mature flower bud size: Length: 18.3 mm. Diameter: 5.5 mm to 6 mm. Shape: Initial visible flower bud has a round ball shape; mature flower. buds have an elongated olive shape.

*Flower petals.*—Length: 21.0 mm. Width: 8.2 mm. Color: RHS 155D (white). Shape: Flat, spatula-shaped. Apex shape: Smooth, acute-shaped. Base shape: Even obtuse. Margin: Smooth.

*Flower sepal.*—Shape: Delta-shaped. Apex shape: Triangle-shaped. Margin: Smooth.

*Fragrance.*—Fragrant/Mostly fragrant.

*Reproductive organs.*—Fertility: Appears self-fertile. Pollen amount: Abundant/moderate amount. Pollen color (general): Bright-yellow. Ovary shape: Oval-shaped.

Fruit:

*Size.*—Uniform.

*Height.*—77 to 83 mm on average.

*Width.*—88.2 to 90 mm on average.

*Average weight* (*per individual fruit*).—275 grams.

*Shape.*—Round.

*Shape* (*cross-section*).—Round.

*Apex.*—Truncated with slight dent.

*Apex cavity diameter.*—N/A.

*Base cavity diameter.*—5.8 to 7.0 mm.

*Base.*—No neck.

*Harvesting*.—Fruit can be harvested from October through December in Florida, although fruit continue to hold on the tree for a longer time.

*Fruit stem* (*short stem connecting the fruit*).—Length: 10 mm. Diameter: 5.6 mm. Color: RHS 197A (greyed-green) with RHS 138C (green) strip.

Rind:

*Adherence*.—Adherence between albedo (mesocarp) and flesh (endocarp) is medium. The adherence is evenly distributed from base to apex.

*Thickness*.—3.4 to 3.8 mm on average.

*Texture*.—Smooth.

*Color*.—Flavedo (epicarp): Ranges between RHS N144B (yellow-green) to RHS 150C (yellow-green). Albedo (mesocarp): RHS 155C (white).

*Stylar end*.—Closed.

*Rind oil cell density*.—100-105 oil cells/square cm.

Flesh:

*Number of segments*.—Between 10 and 11 segments per fruit on average.

*Segment walls*.—Medium-soft with sufficient strength to maintain integrity as separated.

*Juice*.—Abundant.

*Color*.—Uniformly RHS 151D (yellow-green).

*Texture*.—Medium soft.

*Vesicles*.—Length: Arranged from 14.2 to 15.6 mm on average. Diameter (thickness): 3.8 to 4.6 mm on average.

*Eating quality*.—N/A.

*Juice index*.—Soluble solids (average): 9.2 Brix.

Seeds:

*Type*.—Polyembryonic and monoembryonic

*Number*.—Ranges from 18 to 26.

*Shape*.—Seed shapes are not uniform. Normal seeds are mostly ventricose/swollen-shaped and clavate/club-shaped.

*Size*.—Length: 15 to 21.5 mm. Width: 8.5 to 10.9 mm.

*Seed coat color*.—Outer Surface: RHS 155A (white) and wrinkled. Inner surface: RHS 165B (greyed-orange). Cotyledon color: RHS NN155A (white).

Resistance to disease: 'UFR-17' rootstock was selected on the basis of its positive reaction to HLB disease (huang-longbing or *citrus* greening disease) in multiple field trials. Trees on this rootstock show a reduced frequency of infection and reduced disease symptoms once infected as compared to commercial diploid rootstocks.

Temperature tolerance: 'UFR-17' demonstrated tolerance to Florida heat at multiple locations. Young sweet orange trees on 'UFR-17' survived two freezes better than several other rootstocks in a trial near Dundee, Fla.

What is claimed is:

1. A new and distinct *citrus* rootstock cultivar as illustrated and described herein.

* * * * *